(12) United States Patent
Harrison et al.

(10) Patent No.: US 11,823,379 B2
(45) Date of Patent: Nov. 21, 2023

(54) USER-GUIDED DOMAIN ADAPTATION FOR RAPID ANNOTATION FROM USER INTERACTIONS FOR PATHOLOGICAL ORGAN SEGMENTATION

(71) Applicant: Ping An Technology (Shenzhen) Co., Ltd., Shenzhen (CN)

(72) Inventors: Adam P Harrison, Bethesda, MD (US); Ashwin Raju, Bethesda, MD (US)

(73) Assignee: PING AN TECHNOLOGY (SHENZHEN) CO., LTD., Shenzhen (CN)

(*) Notice: Subject to any disclaimer, the term of this patent is extended or adjusted under 35 U.S.C. 154(b) by 423 days.

(21) Appl. No.: 17/138,251

(22) Filed: Dec. 30, 2020

(65) Prior Publication Data
US 2022/0044394 A1    Feb. 10, 2022

Related U.S. Application Data

(60) Provisional application No. 63/061,555, filed on Aug. 5, 2020.

(51) Int. Cl.
G06T 7/00 (2017.01)
G06T 7/33 (2017.01)
G16H 30/40 (2018.01)

(52) U.S. Cl.
CPC .......... G06T 7/0012 (2013.01); G06T 7/344 (2017.01); G16H 30/40 (2018.01);
(Continued)

(58) Field of Classification Search
CPC .............. G06T 7/0012; G06T 7/344; G06T 2207/20081; G06T 2207/20084; G06T 2207/30056; G16H 30/40
See application file for complete search history.

(56) References Cited

U.S. PATENT DOCUMENTS

| | | | |
|---|---|---|---|
| 10,643,130 B2* | 5/2020 | Fidler | G06N 3/084 |
| 10,943,352 B2* | 3/2021 | Sun | G06V 10/82 |
| 2019/0057515 A1* | 2/2019 | Teixeira | G06T 7/50 |

(Continued)

OTHER PUBLICATIONS

Li, Hongwei, et al. "Domain adaptive medical image segmentation via adversarial learning of disease-specific spatial patterns." arXiv preprint arXiv:2001.09313 (2020) (Year: 2020).*

(Continued)

*Primary Examiner* — Amandeep Saini
*Assistant Examiner* — Julius Chai
(74) *Attorney, Agent, or Firm* — ANOVA LAW GROUP, PLLC

(57) ABSTRACT

The present disclosure provides a computer-implemented method, a device, and a computer program product using a user-guided domain adaptation (UGDA) architecture. The method includes training a combined model using a source image dataset by minimizing a supervised loss of the combined model to obtain first sharing weights for a first FCN and second sharing weights for a second FCN; training a discriminator by inputting extreme-point/mask prediction pairs for each of the source image dataset and a target image dataset and by minimizing a discriminator loss to obtain discriminator weights; and finetuning the combined model by predicting extreme-point/mask prediction pairs for the target image dataset to fool the discriminator by matching a distribution of the extreme-point/mask prediction pairs for the target image dataset with a distribution of the extreme-point/mask prediction pairs for the source image dataset.

19 Claims, 3 Drawing Sheets

(52) U.S. Cl.
CPC .............. *G06T 2207/20081* (2013.01); *G06T 2207/20084* (2013.01); *G06T 2207/30056* (2013.01)

(56) References Cited

U.S. PATENT DOCUMENTS

| | | | | |
|---|---|---|---|---|
| 2021/0019629 | A1* | 1/2021 | Chidlovskii | G06V 10/764 |
| 2021/0366123 | A1* | 11/2021 | Wang | G06V 10/82 |
| 2022/0245793 | A1* | 8/2022 | Gilbert | G06T 7/11 |

OTHER PUBLICATIONS

Girum, Kibrom Berihu, et al. "A deep learning method for real-time intraoperative US image segmentation in prostate brachytherapy." International Journal of Computer Assisted Radiology and Surgery 15.9 (2020): 1467-1476 (Year: 2020).*

Tsai, Yi-Hsuan, et al. "Learning to Adapt Structured Output Space for Semantic Segmentation." arXiv preprint arXiv:1802.10349 (2018) (Year: 2018).*

Roth, Holger, et al. "Weakly supervised segmentation from extreme points." Large-Scale Annotation of Biomedical Data and Expert Label Synthesis and Hardware Aware Learning for Medical Imaging and Computer Assisted Intervention: International Workshops, Labels 2019, HAL-MICCAI 2019, and CuRIOUS 2019 (Year: 2019).*

X. Xu, F. Meng, H. Li, Q. Wu, Y. Yang and S. Chen, "Bounding Box based Annotation Generation for Semantic Segmentation by Boundary Detection," 2019 International Symposium on Intelligent Signal Processing and Communication Systems (ISPACS), Taipei, Taiwan, 2019, pp. 1-2, doi: 10.1109/ISPACS48206.20 (Year: 2019).*

Dou, Qi, et al. "Unsupervised cross-modality domain adaptation of convnets for biomedical image segmentations with adversarial loss." arXiv preprint arXiv:1804.10916 (2018) (Year: 2018).*

Maninis, Kevis-Kokitsi, et al. "Deep extreme cut: From extreme points to object segmentation." Proceedings of the IEEE Conference on Computer Vision and Pattern Recognition. 2018. (Year: 2018).*

C. Ruan, W. Wang, H. Hu and D. Chen, "Category-Level Adversaries for Semantic Domain Adaptation," in IEEE Access, vol. 7, pp. 83198-83208, 2019, doi: 10.1109/ACCESS.2019.2921030. (Year: 2019).*

Wang, Guotai, et al. "DeepIGeoS: a deep interactive geodesic framework for medical image segmentation." IEEE transactions on pattern analysis and machine intelligence 41.7 (2018): 1559-1572. (Year: 2018).*

* cited by examiner

USER-GUIDED DOMAIN ADAPTATION FOR RAPID ANNOTATION FROM USER INTERACTIONS FOR PATHOLOGICAL ORGAN SEGMENTATION

CROSS-REFERENCE TO RELATED APPLICATION

This application claims the priority of U.S. Provisional Patent Application No. 63/061,555, filed on Aug. 5, 2020, the entire content of which is incorporated herein by reference.

FIELD OF THE DISCLOSURE

The present disclosure generally relates to the field of domain adaptation technology and, more particularly, relates to a method, a device, and a computer program product for medical image annotation using a user-guided domain adaptation (UGDA) architecture.

BACKGROUND

Reliable computer-assisted segmentation of anatomical structures from medical images can allow for quantitative biomarkers for disease diagnosis, prognosis, and progression. Given the extreme labor to fully annotate data, especially for 3D volumes, a considerable body of work focuses on weakly-supervised segmentation solutions. Solutions that can leverage user interactions (UIs), including extreme points, scribbles, and boundary marks, are an important such category.

The main challenge is effectively leveraging UIs to constrain or guide the mask generation. Classic approaches, like the random walker (RW) algorithm, may be performed via propagating seed regions using intensity similarities. With the advent of deep-learning, harmonizing mask predictions with the UIs continues to be a challenge. Deep extreme points (DEXTR), which requires the user to click on the extreme boundary points of an object, is a popular and effective approach. However, DEXTR only adds the extreme point annotations as an additional channel when training a segmentor, meaning the predicted mask may not agree with the UIs. Therefore, there is a need to develop a rapid annotation method using minimal-labor user interactions to enhance mask predictions or generations on a target dataset or a deployment scenario.

BRIEF SUMMARY OF THE DISCLOSURE

One aspect or embodiment of the present disclosure provides a computer-implemented user-guided domain adaptation (UGDA) method for medical image annotation. The method includes using a labelled source image dataset of medical images, training a combined model, including a first fully convolutional network (FCN) and a second FCN chained with the first FCN, by minimizing a supervised loss of the combined model to obtain one or more first sharing weights for the first FCN and one or more second sharing weights for the second FCN; using the combined model to generate extreme-point predictions, based on the one or more first sharing weights, and generate mask predictions, based on the one or more second sharing weights, for each of the source image dataset and a target image dataset; training a discriminator by inputting extreme-point/mask prediction pairs for each of the source image dataset and the target image dataset and by minimizing a discriminator loss to obtain one or more discriminator weights; and finetuning the combined model by predicting extreme-point/mask prediction pairs for the target image dataset to fool the discriminator having the one or more discriminator weights and matching a distribution of the extreme-point/mask prediction pairs for the target image dataset with a distribution of the extreme-point/mask prediction pairs of the source image dataset.

Optionally, predicting the extreme-point/mask prediction pairs for the target image dataset includes obtaining the extreme-point predictions of the target image dataset; and using the obtained extreme-point predictions as anchors to obtain mask predictions thereof, where an adversarial loss is used to guide the mask predictions to properly align with the obtained extreme-point predictions.

Optionally, the adversarial loss is computed according to:

$$\mathcal{L}_{adv} = \frac{1}{N_t}\sum_{D_t} \ell_{bce}(d(\{\check{Y}, \check{E}\}), 1))$$

where $\mathcal{L}_{adv}$ denotes the adversarial loss, $\ell_{bce}$ denotes a cross-entropy loss; $N_t$ denotes cardinality of the target image dataset; $D_t$ denotes a volume of the target image dataset; $\check{Y}$ and $\check{E}$ denote the mask predictions and the extreme-point predictions; and 1 denotes a label indicating the extreme-point/mask prediction pairs come from the source image dataset.

Optionally, the first FCN is configured to predict extreme points which are inputted into the second FCN; and the second FCN is configured to predict masks based on the extreme-point predictions of the first FCN.

Optionally, the supervised loss is calculated based on an extreme-point loss and a segmentation loss.

Optionally, the discriminator loss is computed according to:

$$\mathcal{L}_d = \frac{1}{N_s}\sum_{D_s} \ell_{bce}(d(\{\check{Y}, \check{E}\}), 1)) + \frac{1}{N_t}\sum_{D_t} \ell_{bce}(d(\{\check{Y}, \check{E}\}), 0))$$

where $\mathcal{L}_d$ denotes the discriminator loss; $\ell_{bce}$ denotes a cross-entropy loss; $N_s$ denotes cardinality of the source image dataset; $N_t$ denotes cardinality of the target image dataset; $D_s$ denotes a volume of the source image dataset; $D_t$ denotes a volume of the target image dataset; $\check{Y}$ and $\check{E}$ denote the mask predictions and the extreme-point predictions; and 0 and 1 denote labels indicating the extreme-point/mask prediction pairs come from the target image dataset and the source image dataset, respectively.

Optionally, the overall training for the UGDA method is to minimize a total loss which is computed according to the supervised loss and the adversarial loss.

Optionally, the source image dataset includes volumes for pathological and healthy organs; and the target image dataset includes volumes for pathological organs, with etiologies/characteristics unseen in the source image dataset.

Optionally, the first FCN outputs a plurality of Gaussian heatmaps to the second FCN for predicting one mask, each Gaussian heatmap corresponding to one extreme point.

Optionally, the target image dataset includes both user interaction (UI)-labelled and un-labelled volumes; and the source image dataset includes fully supervised volumes with masks.

Another aspect or embodiment of the present disclosure provides a device for user-guided domain adaptation (UGDA). The device includes a memory, containing a computer program stored thereon; and a processor, coupled with the memory and configured, when the computer program being executed, to perform a method including: using a labelled source image dataset of medical images, training a combined model, including a first fully convolutional network (FCN) and a second FCN chained with the first FCN, by minimizing a supervised loss of the combined model to obtain one or more first sharing weights for the first FCN and one or more second sharing weights for the second FCN; using the combined model to generate extreme-point predictions, based on the one or more first sharing weights, and generate mask predictions, based on the one or more second sharing weights, for each of the source image dataset and a target image dataset; training a discriminator by inputting extreme-point/mask prediction pairs for each of the source image dataset and the target image dataset and by minimizing a discriminator loss to obtain one or more discriminator weights; and finetuning the combined model by predicting extreme-point/mask prediction pairs for the target image dataset to fool the discriminator having the one or more discriminator weights and matching a distribution of the extreme-point/mask prediction pairs for the target image dataset with a distribution of the extreme-point/mask prediction pairs of the source image dataset.

Optionally, predicting the extreme-point/mask prediction pairs for the target image dataset includes obtaining the extreme-point predictions of the target image dataset; and using the obtained extreme-point predictions as anchors to obtain mask predictions thereof, where an adversarial loss is used to guide the mask predictions to properly align with the obtained extreme-point predictions.

Optionally, the first FCN is configured to predict extreme points which are inputted into the second FCN; and the second FCN is configured to predict masks based on the extreme-point predictions of the first FCN.

Optionally, the first FCN outputs a plurality of Gaussian heatmaps to the second FCN for predicting one mask, each Gaussian heatmap corresponding to one extreme point.

Another aspect or embodiment of the present disclosure provides a computer program product including a non-transitory computer-readable storage medium and program instructions stored therein, the program instructions being configured to be executable by a computer to cause the computer to implement operations including: using a labelled source image dataset of medical images, training a combined model, including a first fully convolutional network (FCN) and a second FCN chained with the first FCN, by minimizing a supervised loss of the combined model to obtain one or more first sharing weights for the first FCN and one or more second sharing weights for the second FCN; using the combined model to generate extreme-point predictions, based on the one or more first sharing weights, and generate mask predictions, based on the one or more second sharing weights, for each of the source image dataset and a target image dataset; training a discriminator by inputting extreme-point/mask prediction pairs for each of the source image dataset and the target image dataset and by minimizing a discriminator loss to obtain one or more discriminator weights; and finetuning the combined model by predicting extreme-point/mask prediction pairs for the target image dataset to fool the discriminator having the one or more discriminator weights and matching a distribution of the extreme-point/mask prediction pairs for the target image dataset with a distribution of the extreme-point/mask prediction pairs of the source image dataset.

Optionally, predicting the extreme-point/mask prediction pairs for the target image dataset includes obtaining the extreme-point predictions of the target image dataset; and using the obtained extreme-point predictions as anchors to obtain mask predictions thereof, where an adversarial loss is used to guide the mask predictions to properly align with the obtained extreme-point predictions.

Optionally, the first FCN is configured to predict extreme points which are inputted into the second FCN; and the second FCN is configured to predict masks based on the extreme-point predictions of the first FCN.

Optionally, the first FCN outputs a plurality of Gaussian heatmaps to the second FCN for predicting one mask, each Gaussian heatmap corresponding to one extreme point.

Other aspects or embodiments of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Figure 1:
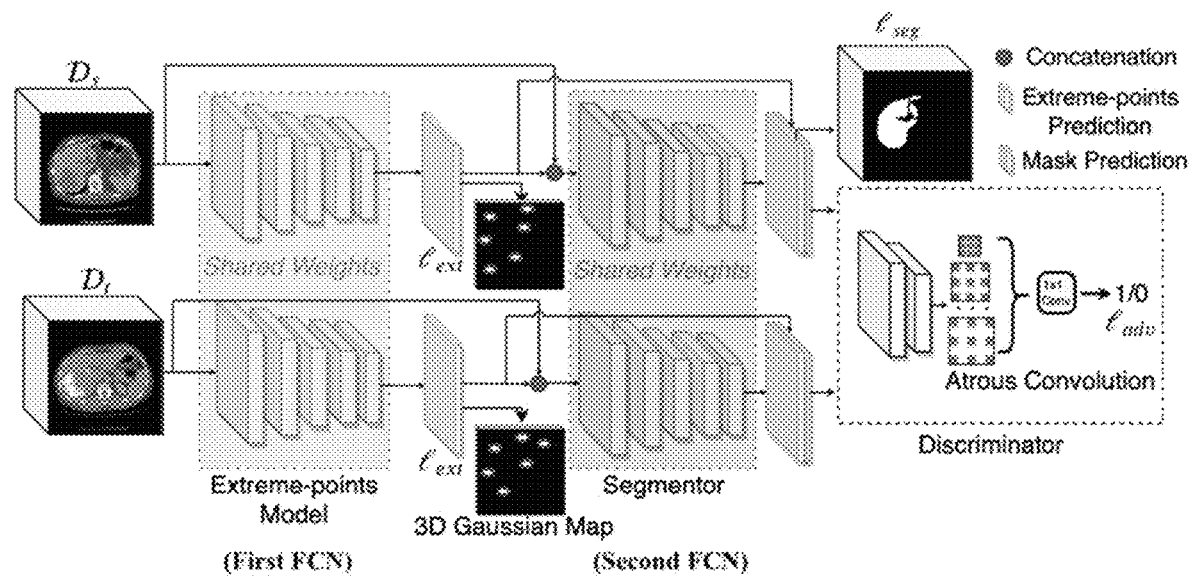
FIG. 1 illustrates an exemplary diagram of a user-guided domain adaptation (UGDA) method according to various disclosed embodiments of the present disclosure.

Reference may be made in detail to exemplary embodiments of the disclosure, which are illustrated in the accompanying drawings. Wherever possible, the same reference numbers may be used throughout the drawings to refer to the same or like parts.

While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, such that an item or items following any one of these words is not meant to be an exhaustive listing of the item or items, or meant to be limited to only the listed item or items. And the singular forms "a," "an," and "the" are intended to include plural references, unless the context clearly dictates otherwise.

Mask-based annotation of medical images, especially for 3D data, is a bottleneck in developing reliable machine learning models. Using minimal-labor user interactions (UIs) to guide the annotation is promising, but challenges remain on best harmonizing the mask prediction with the UIs. UIs may include extreme points, scribbles, boundary marks, and the like. To solve the above-mentioned technical problem, the present disclosure provides a user-guided domain adaptation (UGDA) method, which uses prediction-based adversarial domain adaptation (PADA) to model the combined distribution of UIs and mask predictions. The UIs are then used as anchors to guide and align the mask prediction. Importantly, the UGDA method may both learn from un-labelled data and also model the high-level semantic meaning behind different UIs. Furthermore, it demonstrates that the UGDA method may retain state-of-the-art performance even when only seeing a fraction of available UIs, demonstrating an ability for robust and reliable UI-guided segmentation with extremely minimal labor demands.

The UGDA method may use prediction-based adversarial domain adaptation (PADA) to guide mask predictions by the UIs. The UGDA method's advantage may be that it is equipped to model the high-level meaning behind different types of UIs and how the UIs should impact the ultimate mask prediction. Importantly, the UIs are used as anchors when adapting the mask. Another advantage may be that, like PADA, the UGDA method can learn from and exploit completely un-labelled data, in addition to data accompanied by UIs. Without loss of generality, it is focused on using DEXTR-style extreme-point UIs because of intuitiveness and effectiveness in the embodiments of the present disclosure. However, other UI types, e.g., boundary corrections, are equally possible in addition to, or instead of, extreme points. One constraint is that a fully supervised dataset is assumed to be available in order to model the interplay between masks and UIs. However, such data can originate from sources other than a target dataset, for example, from public data.

Various embodiments provide a method, a device, and a computer program product for medical image annotation using user-guided domain adaptation (UGDA) for pathological organ segmentation. Any organ of interest may be applied to the disclosed method, device and computer program product, although the present disclosure is described using liver as an example of organ for illustrative purposes.

FIG. 1 illustrates an exemplary diagram of a user-guided domain adaptation (UGDA) method according to various disclosed embodiments of the present disclosure. Referring to FIG. 1, reliable mask predictions may be produced on a target image dataset or deployment scenario, given only minimal UIs. More formally, it is assumed that the target image dataset composed of both UI-labelled and completely un-labelled volumes is given: $D_t = \{X_i, E_i\}_{i=1}^{N_s} \cup \{X_i\}_{i=1}^{N_u}$, with $X_i$ and $E_i$ denoting images and extreme-point UIs, respectively. In addition, it is assumed that a fully supervised source image dataset with masks is also available, $D_s = \{X_i, Y_i\}_{i=1}^{N_s}$. As long as the masks and extreme points describe the same anatomical structure, $D_s$ may originate from entirely different sources, for example, public data. The UGDA method (e.g., algorithm or framework) shown in FIG. 1 may be configured to efficiently and effectively exploit the extreme-point UIs.

Referring to FIG. 1, the UGDA method may chain together a first (or initial) FCN (fully convolutional network), which predicts the extreme points of an object (e.g., image), with a second FCN, which accepts the extreme-point predictions from the first FCN to predict a mask. For the source image dataset, $D_s$, where the mask label is present, a fully supervised loss may be computed on both the extreme-point predictions and the mask predictions. For the target image dataset, $D_t$, the fully supervised loss may be computed when UIs are available. For all $D_t$ volumes, whether UI-labelled or completely un-labelled, PADA may be used to guide the mask predictions based on the extreme-point anchors.

Supervised Workflow (or Training)

The backbone of the UGDA method may have two 3D FCNs chained together, where the first FCN (i.e., the extreme-point model) predicts extreme points while the second FCN (i.e., the segmentation model or segmentor) predicts a full mask. Working backward, the second FCN may act similarly to DEXTR, where the second FCN predicts a mask given an input image along with the extreme-point UIs as the following:

$$\check{Y} = s(X, E) \quad (1)$$

where s(.) is used to represent the second (i.e., segmentation) FCN.

Each of a plurality of (e.g., 6) extreme points may be represented by a 3D Gaussian heatmap centered on user clicks and rendered into an additional input channel $E_i$. It is found that the UGDA method may not be sensitive to the size of the Gaussian heatmaps, and a kernel with 5-pixel standard deviation may be used according to the embodiments of the present disclosure. However, unlike DEXTR, it is not assumed that all training volumes come with extreme points, as only certain target volumes in $D_t$ have UIs including extreme points.

In order to solve the above-mentioned problem, the first FCN may be used to predict extreme-point heatmaps for each volume. Following heatmap regression conventions, the first FCN (i.e., the extreme-point model) h(.) may output six 3D Gaussian heatmaps, each corresponding to one extreme point. The six 3D Gaussian heatmaps may be then summed together into one channel prior to being inputted into the second FCN (i.e., the segmentation model or segmentor) as the following:

$$\check{Y} = s(X, \check{E}) \quad (2)$$

$$\check{E} = h(X) \quad (3)$$

where the summation of 6 heatmaps into one channel may be skipped for convenience. By relying on above-mentioned predictions, the present method may be allowed to operate even with un-labelled image data.

In terms of loss, if $D_e$ is used to denote any input volume associated with extreme-point UIs, whether from $D_s$ or $D_t$, then a supervised loss may be formulated as:

$$\mathcal{L}_{sup} = \mathcal{L}_{seg} + \mathcal{L}_{ext} \quad (4)$$

$$\mathcal{L}_{ext} = \frac{1}{N_e} \sum_{X, E \in D_e} \ell_{ext}(h(X), E) \quad (5)$$

$$\mathcal{L}_{seg} = \frac{1}{N_s} \sum_{X, Y \in D_s} \ell_{seg}(s(X, h(X)), Y) \quad (6)$$

where $\mathcal{L}_{sup}$ denotes the supervised loss; $\mathcal{L}_{seg}$ denotes a segmentation loss of the second FCN; $\mathcal{L}_{ext}$ denotes an extreme-point loss of the first FCN; $N_e$ denotes the cardinality of $D_e$; $N_s$ denotes the cardinality of $D_s$; $\ell_{ext}$ denotes a mean-squared error; and $\ell_{seg}$ denotes a summation of cross entropy and Dice-Sorensen coefficient (DSC) losses.

While focusing on extreme points at the present disclosure, other types of UIs, such as boundary corrections, may be readily incorporated in above-mentioned method according to the embodiments of the present disclosure.

User-Guided Domain Adaptation

Similar to DEXTR, equation (6) may indirectly guide mask predictions by using extreme-point heatmaps as an additional input channel for the second FCN. Additionally, for UI-labelled volumes in $D_t$, the supervised loss in equation (5) may encourage the extreme-point predictions to actually match the UIs (e.g., labeled or actual extreme points). However, the mask prediction may contradict the UIs because there is no penalty for disagreement between the mask prediction and the UIs. Thus, an additional mechanism may be needed to align the mask with UIs. An adversarial domain adaption approach may be selected to penalize discordant mask predictions. While image translation-based adversarial domain adaptation methods show desirable results, such methods may be unsuited to the present task because it is concerned with adapting the prediction-space to produce a mask well-aligned with the UIs. Therefore, prediction-based adversarial domain adaptation (PADA) may be used in the present disclosure.

In some embodiments of the present disclosure, a discriminator d(.) may be used to learn the distribution and interplay between mask predictions and extreme-point predictions. Treating samples from $D_s$ as the "correct" distribution, the discriminator loss may be expressed as:

$$\mathcal{L}_d = \frac{1}{N_s}\sum_{D_s}\ell_{bce}(d(\{\check{Y}, \check{E}\}, 1)) + \frac{1}{N_t}\sum_{D_t}\ell_{bce}(d(\{\check{Y}, \check{E}\}, 0)) \quad (7)$$

where $\mathcal{L}_d$ denotes the discriminator loss; $\ell_{bce}$ denotes a cross-entropy loss; $N_s$ denotes cardinality of the source image dataset; $N_t$ denotes cardinality of the target image dataset; $D_s$ denotes a volume of the source image dataset; $D_t$ denotes a volume of the target image dataset; $\check{Y}$ and $\check{E}$ denote the mask predictions and the extreme-point predictions; and 0 and 1 denote labels indicating the extreme-point/mask predictions come from the target and source image datasets, respectively. The discriminator loss may be set up to encourage the discriminator to correctly discern whether predictions come from the source image dataset or the target image dataset.

Importantly, to model the combined distribution, the discriminator may accept both the UIs and mask predictions. Following standard adversarial training, gradients may only flow through the discriminator herein. UGDA then may attempt to fool the discriminator by predicting extreme point/mask pairs for $D_t$ that match the distribution of $D_s$. More formally, an adversarial loss is set up for volumes in $D_t$ as the following:

$$\mathcal{L}_{adv} = \frac{1}{N_t}\sum_{D_t}\ell_{bce}(d(\{\check{Y}, \check{E}\}, 1)) \quad (8)$$

where $\mathcal{L}_{adv}$ denotes the adversarial loss; $\ell_{bce}$ denotes a cross-entropy loss; $N_t$ denotes cardinality of the target image dataset; $D_t$ denotes a volume of the target image dataset; $\check{Y}$ and $\check{E}$ denote the mask predictions and the extreme-point predictions; and 1 denotes a label indicating the extreme-point/mask pair which (erroneously) comes from the source distribution (e.g., the source image dataset). The adversarial loss may encourage the combined model to produce extreme-point/mask predictions for the target image dataset that can fool the discriminator in thinking such extreme-point/mask predictions come from the source image dataset.

It should be noted that, compared to equation (7), the "label" for $D_t$ has been switched from 0 to 1. Like standard PADA setups, gradients may not flow through the discriminator weights in equation (8). Importantly, gradients also may not flow through the extreme-point predictions when the UIs are present. Consequently, when UIs are available, extreme-point predictions may only be influenced by the supervised loss in equation (5) to match the UIs. Thus, the extreme-point predictions may act as anchors, while the adversarial loss in equation (8) may guide the mask predictions to properly align with the UIs. Such alignment may be more than simply making mask predictions agree with the UIs, as by modelling the interplay, PADA may also guide mask regions far away from UIs. Finally, the use of PADA may provide another important benefit, as completely unlabelled volumes in $D_t$ may seamlessly contribute to the learning process in equations (7) and (8). In fact, UGDA may be seen as integrating domain adaptation learning processes in addition to DEXTR-style guidance from UIs. Thus, the overall training objective for the UGDA method may be to minimize the following total loss:

$$\mathcal{L} = \mathcal{L}_{sup} + \lambda_{adv}\mathcal{L}_{adv} \quad (9)$$

where $\lambda_{adv}$ is a weight used to balance the supervised loss and the adversarial loss; and the loss weighting is kept to only the adversarial component to reduce hyper-parameter tuning.

In some embodiments of the present disclosure, the UGDA method may be tested on segmenting pathological organs of interest (for example, livers), using the target image dataset ($D_t$) of 927 venous-phase computed tomography (CT) studies from the picture archiving and communication system (PACS) of Chang Gung Memorial hospital (CGMH). The selection criterion may be of patients with bio-spied or resected liver lesions, with CT scans taken within one month before the procedure. Patients may directly reflect clinical distributions and represent hepatocellular carcinoma (HCC), intrahepatic cholangiocellular carcinoma (ICC), benign or metastasized lesions, along with co-occurring maladies, such as liver fibrosis, splenomegaly, or embolized lesions. From the above-mentioned image dataset, 47 and 100 studies may be selected as validation and test sets, respectively, to delineate the patient livers. The above-mentioned 147 CTs may be named as evaluation volumes. The remainder of the above-mentioned image dataset may be annotated using only extreme-point UIs. The source image dataset $D_s$ may include collected 235 fully labelled venous-phase CT studies from public datasets, which, unlike $D_t$, includes both healthy and pathological livers and only represents HCC and metastasized tumors. Corresponding extreme-point "UIs" may be generated from the full masks. For internal validation, the source dataset $D_s$ may be split into 70%, 20%, and 10% for training, testing, and validation, respectively.

In some embodiments of the present disclosure, a 3D version of the deeply supervised progressive holistically nested network (PHNN), which provides an efficient and decoder-free pipeline, may be configured for two FCN architectures of the UGDA method. For example, a fully supervised baseline on $D_s$ may be first trained using equation (4), which may then be finetuned after convergence using equation (9). The dual-PHNN baseline may be very strong on the public data used, achieving a DSC score of about 96.9% on the $D_s$ test set. For the discriminator, a 3D version of a popular architecture using atrous convolution may be configured, which has proved a useful discriminator for liver masks.

In some embodiments of the present disclosure, the UGDA method may be evaluated on how well it can annotate $D_t$ using only extreme-point UIs. The evaluation volumes and their extreme-point UIs may be included within the training procedure, but the corresponding masks may be hidden. For the evaluation, DSC scores and the mask-extreme-point agreement (MXA) may be measured. The MXA may measure the average distance between all six of a predicted mask's extreme-points versus the ground-truth extreme points. In such way, it may directly measure how well the method (e.g., the combined model) can produce a mask prediction that actually matches the extreme-point UIs.

Table. 1 outlines the performance of all variants in annotating $D_t$. It can be seen that, compared to its performance on $D_s$, the fully supervised dual PHNN's performance drops from about 96.9% to about 93.0% due to the major differences between public liver datasets and the PACS-based clinical target dataset used.

TABLE 1

DSC and MXA mean, standard deviation scores, and the fraction of UI-labelled $D_t$ volumes used for training

| Model | % UIs | DSC | MXA (mm) |
|---|---|---|---|
| Dual PHNN | N/A | 93.0 ± 3.2 | 4.3 ± 1.2 |
| DEXTR | 100% | 93.1 ± 2.4 | 3.9 ± 1.2 |
| Mask-based PADA (no UIs) | 0% | 94.8 ± 1.8 | 3.4 ± 1.6 |
| Mask-based PADA (w UIs) | 100% | 95.5 ± 1.0 | 2.5 ± 1.0 |
| UGDA | 25% | 95.8 ± 0.8 | 1.7 ± 0.8 |
| UGDA | 50% | 96.0 ± 0.9 | 1.4 ± 0.9 |
| UGDA | 100% | 96.1 ± 0.8 | 1.1 ± 0.9 |

Referring to Table 1, by exploiting UIs, DEXTR may significantly boost the MXA, but its undesirable DSC scores may suggest that the resulting masks, while aligning better with the extreme points, still may not properly capture the liver extent. On the other hand, both mask-based PADA variants perform better than PHNN and DEXTR, indicating that modelling mask distributions on top of DEXTR-style UI guidance may more robustly annotate $D_t$. Finally, the performance of the UGDA method is highest in all of the above-mentioned models (or methods), demonstrating that modelling the interplay between the UIs and mask predictions may boost performance even further. Importantly, the UGDA method's MXA is significantly desirable (e.g., 1.1 mm), which may indicate that the mask predictions well match the UIs.

Figure 2:
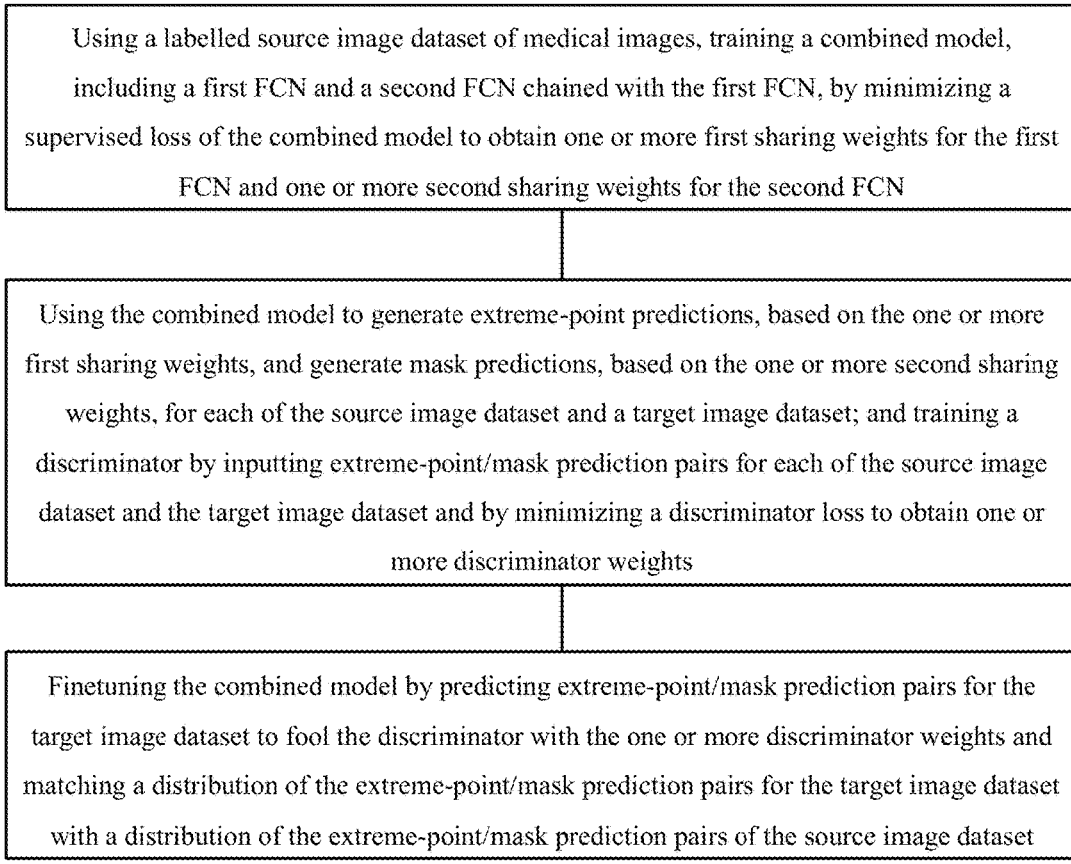
FIG. 2 illustrates a flowchart for an exemplary training process of a user-guided domain adaptation (UGDA) method according to various disclosed embodiments of the present disclosure.

FIG. 2 illustrates an exemplary training process flowchart for the user-guided domain adaptation (UGDA) method according to various disclosed embodiments of the present disclosure.

At S202, the medical images of the labelled source image dataset ($D_s$) may be used to train a combined model, thereby obtaining one or more first sharing weights for the first FCN and one or more second sharing weights for the second FCN by minimizing the supervised loss of the combined model. The combined model may include the first FCN (e.g., the extreme-point model) and the second FCN (e.g., the segmentation model or segmentor). The supervised loss ($\mathcal{L}_{sup}$) may be calculated based on the extreme-point loss ($\mathcal{L}_{ext}$) and the segmentation loss ($\mathcal{L}_{seg}$). In the exemplary UGDA method of the present disclosure, the first FCN may be chained with the second FCN as the backbone of the UGDA method, where h(.) is used to represent the first FCN which output six Gaussian heatmaps, each corresponding to one extreme point; and s(.) is used to represent the second FCN which predicts a mask given an input image along with the extreme points. The first FCN may be configured to predict extreme points inputted into the second FCN; and the second FCN may be configured to predict masks based on the extreme-point predictions from the first FCN. The supervised loss ($\mathcal{L}_{sup}$) of the combined model may be computed and minimized to obtain optimized weights of the extreme-points model and the segmentation model (e.g., segmentor). By training the combined model, one or more first sharing weights may be obtained for the first FCN and one or more second sharing weights may be obtained for the second FCN.

In one embodiment of the present disclosure, the combined model may have two FCNs including the first FCN and the second FCN set up in two stages. The first stage's contribution is to produce extreme-point predictions (e.g., UI-based predictions) given an input image. The combined model may also permit other minimal-labor UIs including scribbles or boundary corrections. The second stage's contribution is to produce a mask prediction given the same input image and the first stage's extreme-point predictions. It's significantly easy to obtain UI-based supervision like extreme-point predictions, so that the first stage may be trained from the target image dataset and/or the source image dataset. However, mask predictions are more difficult to obtain, so that the second FCN may be trained only with ground truth masks using the source image dataset.

After the combined model is trained at S202, S204 may be proceeded. At S204, the combined model may be used to generate extreme-point predictions based on the one or more first sharing weights, and generate mask predictions based on one or more the second sharing weights, for each of the source image dataset and the target image dataset, respectively.

According to the combined model of the present disclosure, extreme-point/mask prediction pairs (or prediction pairs), including the extreme-point predictions and the mask predictions, for the source image dataset and for the target image dataset may be inputted into the discriminator. The discriminator may be trained to obtain a minimum discriminator loss $\mathcal{L}_d$ using equation (7), such that one or more discriminator weights may be optimized.

At S206, the combined model may be finetuned by predicting extreme-point/mask prediction pairs for the target image dataset to fool the discriminator having the one or more discriminator weights and matching the distribution of the extreme-point/mask prediction pairs for the target image dataset with the distribution of the extreme-point/mask prediction pairs of the source image dataset. In some embodiments of the present disclosure, using the extreme-point predictions of the target image dataset as anchors, the adversarial loss shown in equation (8) may be used to guide the mask predictions to properly align with the extreme-point predictions, thereby annotating the target image dataset.

In one embodiment, to model the interplay between the extreme-point predictions and the corresponding mask, the extreme-point predictions and the corresponding mask may both be inputted as pairs into the adversarial learning process, and such process may be used to generate masks that better align with the extreme-point predictions. Therefore, technically, the extreme-point predictions may be inputted into the discriminator and then used as anchors. However, when labeled (e.g., actual) extreme points (UIs) are available, the extreme-point predictions themselves may be directly supervised by the labeled extreme points, so that the labeled extreme points would then indirectly act as anchors to the mask predictions.

In various embodiments of the present disclosure, the main reason for inputting the extreme-point predictions, for example, instead of the labeled extreme points themselves may include the following. It is not strictly necessary that all data samples in the target image dataset have associated, labeled extreme points. To make the UGDA framework more flexible, it is desirable that the UGDA framework can function properly when only a portion of the target image dataset has extreme-point supervision. Therefore, in order to allow the UGDA framework to still usefully learn from a completely unsupervised target image data, the extreme-point predictions may be inputted into the discriminator. Such extreme-point predictions are not directly supervised by labeled (e.g., actual) extreme points, so that desirable extreme-points may be produced only relied on the accuracy of the first stage FCN alone. These unsupervised data may only have the adversarial loss act upon them. How much (e.g., the extreme-point UI percentage) of the target image dataset needs extreme points for the UGDA framework to work may be evaluated according to various embodiments of the present disclosure.

Figure 3:
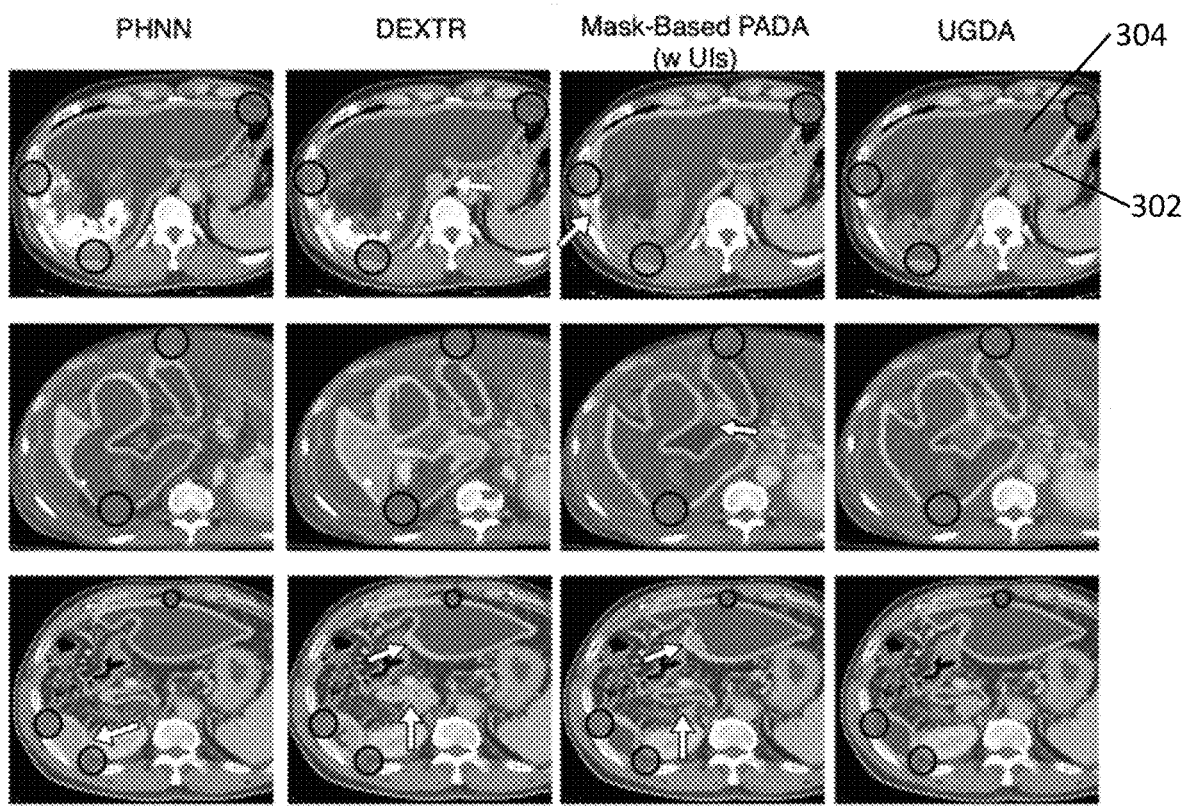
FIG. 3 illustrates exemplary images of liver mask ground truth and predictions for different methods according to various disclosed embodiments of the present disclosure.

FIG. 3 illustrates exemplary images of liver mask ground truth and predictions for different methods according to various disclosed embodiments of the present disclosure. Referring to FIG. 3, liver mask ground truth and predictions are rendered in contour 302 and mask 304, respectively, and Gaussian heatmaps centered on the extreme-point UIs are shown in solid-line black circles. It can be seen that the UGDA method can significantly improve the alignment between the mask predictions and the extreme-point UIs. Arrows may highlight selected baseline prediction errors that the UGDA method corrects. Viewing the qualitative examples in FIG. 3 may reinforce the quantitative improvements. In particular, the UGDA method may be able to ensure that mask predictions both agree with extreme points and provide robust predictions away from the extreme-point UIs.

Figure 4:
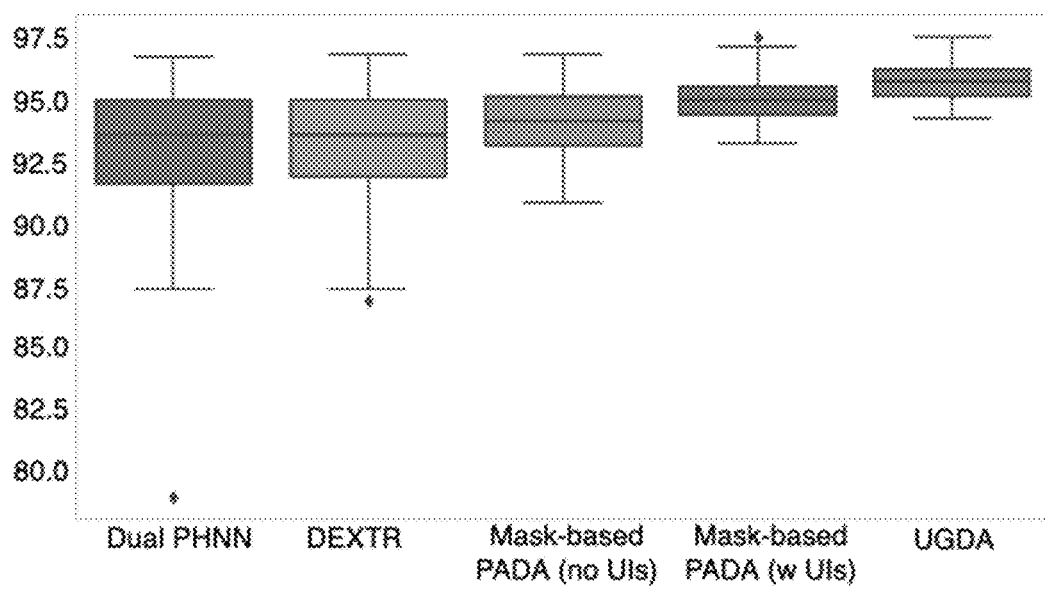
FIG. 4 illustrates a box and whisker plot of pathological liver segmentation Dice-Sorensen coefficient (DSC) scores according to various disclosed embodiments of the present disclosure.

FIG. 4 illustrates a box and whisker plot of pathological liver segmentation Dice-Sorensen coefficient (DSC) scores according to various disclosed embodiments of the present disclosure. The mean MXA scores are bolstered by FIG. 4's box-and-whisker plot, which demonstrate that the UGDA method may provide important boosts in reliability, with an extremely robust worst-case performance of 94.9% DSC, compared to 93.2% for the mask-based PADA (with extreme-point UIs) variant.

Furthermore, the UGDA method may perform almost as well when only a fraction of $D_t$ is UI-labelled, outperforming both DEXTR and the mask-based PADA variant, both of which see all 100% of the extreme-point UIs. These results may indicate that the UGDA method may operate well even in scenarios with extremely minimal UI annotation, providing further evidence of significantly high versatility.

Using only extreme-point UIs, the state-of-the-art mean (worst-case) Dice-Sorensen coefficient (DSC) scores of about 96.1% (94.5%) may be achieved on the above-mentioned image dataset, compared to about 93.0% (79.0%) and about 93.1% (87.0%) for a strong fully-supervised baseline and DEXTR, respectively. It may also demonstrate that the UGDA method may improve over PADA by about 1.3% DSC and even perform robustly when only shown incomplete sets of extreme-point UIs. Finally, it may demonstrate that predicted masks can align extraordinarily well with extreme-point UIs, allowing users to interact with high confidence and minimal frustration.

According to various embodiments of the present disclosure, the UGDA method may enable the mask prediction to be aligned with extreme-point UIs (used as anchors). Importantly, the UGDA method may learn from and exploit completely un-labelled data and model the high-level semantic meaning behind different UIs. Furthermore, the UGDA method may retain high performance even when only seeing a fraction of available UIs, demonstrating an ability for robust and reliable UI-guided segmentation with extremely minimal labor demands.

The present disclosure also provides a device for user-guided domain adaptation (UGDA). The device includes a memory, containing a computer program stored thereon; and a processor, coupled with the memory and configured, when the computer program being executed, to perform a method including: using a labelled source image dataset of medical images, training a combined model, including a first fully convolutional network (FCN) and a second FCN chained with the first FCN, by minimizing a supervised loss of the combined model to obtain one or more first sharing weights for the first FCN and one or more second sharing weights for the second FCN; using the combined model to generate extreme-point predictions, based on the one or more first sharing weights, and generate mask predictions, based on the one or more second sharing weights, for each of the source image dataset and a target image dataset; training a discriminator by inputting extreme-point/mask prediction pairs for each of the source image dataset and the target image dataset and by minimizing a discriminator loss to obtain one or more discriminator weights; and finetuning the combined model by predicting extreme-point/mask prediction pairs for the target image dataset to fool the discriminator with the one or more discriminator weights and matching a distribution of the extreme-point/mask prediction pairs for the target image dataset with a distribution of the extreme-point/mask prediction pairs of the source image dataset.

The present disclosure also provides a computer program product including a non-transitory computer-readable storage medium and program instructions stored therein, the program instructions being configured to be executable by a computer to cause the computer to implement operations including: using a labelled source image dataset of medical images, training a combined model, including a first fully convolutional network (FCN) and a second FCN chained with the first FCN, by minimizing a supervised loss of the combined model to obtain one or more first sharing weights for the first FCN and one or more second sharing weights for the second FCN; using the combined model to generate extreme-point predictions, based on the one or more first sharing weights, and generate mask predictions, based on the one or more second sharing weights, for each of the source image dataset and a target image dataset; training a discriminator by inputting extreme-point/mask prediction pairs for each of the source image dataset and the target image dataset and by minimizing a discriminator loss to obtain one or more discriminator weights; and finetuning the combined model by predicting extreme-point/mask prediction pairs for the target image dataset to fool the discriminator with the one or more discriminator weights and matching a distribution of the extreme-point/mask prediction pairs for the target image dataset with a distribution of the extreme-point/mask prediction pairs of the source image dataset.

While the disclosure has been illustrated with respect to one or more implementations, alterations and/or modifications can be made to the illustrated examples without departing from the spirit and scope of the appended claims. In addition, while a particular feature of the disclosure may have been disclosed with respect to only one of several implementations, such feature may be combined with one or more other features of the other implementations as may be desired and advantageous for any given or particular function. Furthermore, to the extent that the terms "including", "includes", "having", "has", "with", or variants thereof are used in either the detailed description and the claims, such terms are intended to be inclusive in a manner similar to the term "comprising." The term "at least one of" is used to mean one or more of the listed items can be selected.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. In certain cases, the numerical values as stated for the parameter can take on negative values.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A computer-implemented user-guided domain adaptation (UGDA) method for medical image annotation, comprising:
   using a labelled source image dataset of medical images, training a combined model, including a first fully convolutional network (FCN) and a second FCN chained with the first FCN, by minimizing a supervised loss of the combined model to obtain one or more first sharing weights for the first FCN and one or more second sharing weights for the second FCN;
   for each of the source image dataset and a target image dataset,
      using the first FCN of the combined model to generate extreme-point predictions, based on the one or more first sharing weights,
      inputting the extreme-point predictions into the second FCN, and
      using the second FCN to generate mask predictions, based on the one or more second sharing weights and based on the extreme-point predictions generated by the first FCN, thereby obtaining extreme-point/mask prediction pairs for the source image dataset and extreme-point/mask prediction pairs for the target image dataset;
   training a discriminator by inputting the extreme-point/mask prediction pairs for both of the source image dataset and the target image dataset and by minimizing a discriminator loss to obtain one or more discriminator weights; and
   finetuning the combined model by:
      predicting extreme-point/mask prediction pairs for the target image dataset to fool the trained discriminator having the one or more discriminator weights and
      matching a distribution of the extreme-point/mask prediction pairs for the target image dataset with a distribution of the extreme-point/mask prediction pairs of the source image dataset.

2. The method according to claim 1, wherein predicting the extreme-point/mask prediction pairs for the target image dataset includes:
   obtaining the extreme-point predictions of the target image dataset; and
   using the obtained extreme-point predictions as anchors to obtain mask predictions thereof, wherein an adversarial loss is used to guide the mask predictions to properly align with the obtained extreme-point predictions.

3. The method according to claim 2, wherein the adversarial loss is computed according to:

$$\mathcal{L}_{adv} = \frac{1}{N_t} \sum_{D_t} \ell_{bce}(d(\{\check{Y}, \check{E}\}, 1))$$

wherein $\mathcal{L}_{adv}$ denotes the adversarial loss, $\ell_{bce}$ denotes a cross-entropy loss; $N_t$ denotes cardinality of the target image dataset; $D_t$ denotes a volume of the target image dataset; $\check{Y}$ and $\check{E}$ denote the mask predictions and the extreme-point predictions; and 1 denotes a label indicating the extreme-point/mask prediction pairs come from the source image dataset.

4. The method according to claim 3, wherein:
   the overall training for the UGDA method is to minimize a total loss which is computed according to the supervised loss and the adversarial loss.

5. The method according to claim 1, wherein:
   the supervised loss is calculated based on an extreme-point loss and a segmentation loss.

6. The method according to claim 1, wherein the discriminator loss is computed according to:

$$\mathcal{L}_d = \frac{1}{N_s} \sum_{D_s} \ell_{bce}(d(\{\check{Y}, \check{E}\}, 1)) + \frac{1}{N_t} \sum_{D_t} \ell_{bce}(d(\{\check{Y}, \check{E}\}, 0))$$

wherein $\mathcal{L}_d$ denotes the discriminator loss; $\ell_{bce}$ denotes a cross-entropy loss; $N_S$ denotes cardinality of the source image dataset; $N_t$ denotes cardinality of the target image dataset; $D_s$ denotes a volume of the source image dataset; $D_t$ denotes a volume of the target image dataset; $\check{Y}$ and $\check{E}$ denote the mask predictions and the extreme-point predictions; and 0 and 1 denote labels indicating the extreme-point/mask prediction pairs come from the target image dataset and the source image dataset, respectively.

7. The method according to claim 1, wherein:
   the source image dataset includes volumes for pathological and healthy organs; and the target image dataset includes volumes for pathological organs, with etiologies/characteristics unseen in the source image dataset.

8. The method according to claim 1, wherein:
   the first FCN outputs a plurality of Gaussian heatmaps to the second FCN for predicting one mask, each Gaussian heatmap corresponding to one extreme point.

9. The method according to claim 1, wherein:
the target image dataset includes both user interaction (UI)-labelled and un-labelled volumes; and the source image dataset includes fully supervised volumes with masks.

10. A device for user-guided domain adaptation (UGDA), comprising:
a memory, containing a computer program stored thereon; and
a processor, coupled with the memory and configured, when the computer program being executed, to perform a method including:
using a labelled source image dataset of medical images, training a combined model, including a first fully convolutional network (FCN) and a second FCN chained with the first FCN, by minimizing a supervised loss of the combined model to obtain one or more first sharing weights for the first FCN and one or more second sharing weights for the second FCN;
for each of the source image dataset and a target image dataset,
using the first FCN of the combined model to generate extreme-point predictions, based on the one or more first sharing weights,
inputting the extreme-point predictions into the second FCN, and
using the second FCN to generate mask predictions, based on the one or more second sharing weights and based on the extreme-point predictions generated by the first FCN, thereby obtaining extreme-point/mask prediction pairs for the source image dataset and extreme-point/mask prediction pairs for the target image dataset;
training a discriminator by inputting the extreme-point/mask prediction pairs for both of the source image dataset and the target image dataset and by minimizing a discriminator loss to obtain one or more discriminator weights; and
finetuning the combined model by:
predicting extreme-point/mask prediction pairs for the target image dataset to fool the trained discriminator having the one or more discriminator weights and
matching a distribution of the extreme-point/mask prediction pairs for the target image dataset with a distribution of the extreme-point/mask prediction pairs of the source image dataset.

11. The device according to claim 10, wherein predicting the extreme-point/mask prediction pairs for the target image dataset includes:
obtaining the extreme-point predictions of the target image dataset; and
using the obtained extreme-point predictions as anchors to obtain mask predictions thereof, wherein an adversarial loss is used to guide the mask predictions to properly align with the obtained extreme-point predictions.

12. The device according to claim 10, wherein:
the first FCN outputs a plurality of Gaussian heatmaps to the second FCN for predicting one mask, each Gaussian heatmap corresponding to one extreme point.

13. The device according to claim 10, wherein:
the source image dataset includes volumes for pathological and healthy organs; and the target image dataset includes volumes for pathological organs, with etiologies/characteristics unseen in the source image dataset.

14. The device according to claim 10, wherein:
the target image dataset includes both user interaction (UI)-labelled and un-labelled volumes; and the source image dataset includes fully supervised volumes with masks.

15. A computer program product comprising a non-transitory computer-readable storage medium and program instructions stored therein, the program instructions being configured to be executable by a computer to cause the computer to implement operations comprising:
using a labelled source image dataset of medical images, training a combined model, including a first fully convolutional network (FCN) and a second FCN chained with the first FCN, by minimizing a supervised loss of the combined model to obtain one or more first sharing weights for the first FCN and one or more second sharing weights for the second FCN;
for each of the source image dataset and a target image dataset,
using the first FCN of the combined model to generate extreme-point predictions, based on the one or more first sharing weights,
inputting the extreme-point predictions into the second FCN, and
using the second FCN to generate mask predictions, based on the one or more second sharing weights and based on the extreme-point predictions generated by the first FCN, thereby obtaining extreme-point/mask prediction pairs for the source image dataset and extreme-point/mask prediction pairs for the target image dataset;
training a discriminator by inputting the extreme-point/mask prediction pairs for both of the source image dataset and the target image dataset and by minimizing a discriminator loss to obtain one or more discriminator weights; and
finetuning the combined model by:
predicting extreme-point/mask prediction pairs for the target image dataset to fool the trained discriminator having the one or more discriminator weights and
matching a distribution of the extreme-point/mask prediction pairs for the target image dataset with a distribution of the extreme-point/mask prediction pairs of the source image dataset.

16. The product according to claim 15, wherein predicting the extreme-point/mask prediction pairs for the target image dataset includes:
obtaining the extreme-point predictions of the target image dataset; and
using the obtained extreme-point predictions as anchors to obtain mask predictions thereof, wherein an adversarial loss is used to guide the mask predictions to properly align with the obtained extreme-point predictions.

17. The product according to claim 15, wherein:
the first FCN outputs a plurality of Gaussian heatmaps to the second FCN for predicting one mask, each Gaussian heatmap corresponding to one extreme point.

18. The product according to claim 15, wherein:
the source image dataset includes volumes for pathological and healthy organs; and the target image dataset includes volumes for pathological organs, with etiologies/characteristics unseen in the source image dataset.

19. The product according to claim 15, wherein:
the target image dataset includes both user interaction (UI)-labelled and un-labelled volumes; and the source image dataset includes fully supervised volumes with masks.

* * * * *